United States Patent
Kim et al.

(10) Patent No.: US 9,056,143 B2
(45) Date of Patent: Jun. 16, 2015

(54) METHOD FOR PREPARING PELLETS FROM RICE HUSK AND APPARATUS FOR REMOVING ODOR USING RICE HUSK PELLET BIO-MEDIA

(75) Inventors: Kwang-Soo Kim, Goyang-si (KR); Jun-Ho Park, Goyang-si (KR)

(73) Assignees: KOREA INSTITUTE OF CONSTRUCTION TECHNOLOGY, Gyeonggi-do (KR); KEOSUNG CONSTRUCTION CO. LTD, Seoul (KR); KEOSONG CONSTRUCTION CO. LTD, Gyeonggi-do (KR)

( * ) Notice: Subject to any disclaimer, the term of this patent is extended or adjusted under 35 U.S.C. 154(b) by 697 days.

(21) Appl. No.: 12/958,070

(22) Filed: Dec. 1, 2010

(65) Prior Publication Data

US 2011/0159580 A1    Jun. 30, 2011

(30) Foreign Application Priority Data

Dec. 29, 2009    (KR) .................. 10-2009-0132940

(51) Int. Cl.
```
B01J 20/26    (2006.01)
A61L 9/013    (2006.01)
B01D 53/52    (2006.01)
B01D 53/58    (2006.01)
B01D 53/84    (2006.01)
B01J 2/20     (2006.01)
C12M 1/00     (2006.01)
```

(52) U.S. Cl.
CPC ................. *A61L 9/013* (2013.01); *B01D 53/52* (2013.01); *B01D 53/58* (2013.01); *B01D 53/84* (2013.01); *B01D 2251/304* (2013.01); *B01D 2251/606* (2013.01); *B01D 2257/304* (2013.01); *B01D 2257/406* (2013.01); *B01D 2257/90* (2013.01); *B01D 2258/06* (2013.01); *B01J 2/20* (2013.01)

(58) Field of Classification Search
CPC ........ A61L 9/013; B01D 53/52; B01D 53/58; B01D 53/84; B01D 2251/304; B01D 2251/606; B01D 2257/406; B01D 2257/90; B01D 2257/304; B01D 2258/06; B01J 2/20
USPC ....................................... 435/289.1; 502/402
See application file for complete search history.

(56) References Cited

U.S. PATENT DOCUMENTS

| | | | | |
|---|---|---|---|---|
| 5,589,034 | A * | 12/1996 | Hultman et al. | 162/111 |
| 6,069,004 | A | 5/2000 | Teramachi et al. | |
| 6,239,171 | B1 * | 5/2001 | Lane et al. | 514/458 |
| 6,511,844 | B1 | 1/2003 | Smith | |
| 2008/0293927 | A1 * | 11/2008 | Strahm | 530/500 |

FOREIGN PATENT DOCUMENTS

| | | |
|---|---|---|
| JP | 2006517900 | 8/2006 |
| KR | 1019990000002 | 1/1999 |

(Continued)

OTHER PUBLICATIONS

Office Action issued by the United States Patent and Trademark Office for a divisional U.S. Appl. No. 13/911,519 on Apr. 14, 2015.

*Primary Examiner* — Michael Hobbs
(74) *Attorney, Agent, or Firm* — IP & T Group LLP

(57) ABSTRACT

A method for preparing pellets from rice husk includes: grinding rice husk; adding ammonia water to a mixture of ethylene vinyl acetate and poly(vinylacetate) to prepare a mixed liquid binder; mixing the mixed binder with the ground rice husk to obtain a binder/rice husk mixture; extruding the binder/rice husk mixture through an extruder; and cooling the extruded mixture at room temperature.

4 Claims, 4 Drawing Sheets

(56) References Cited

FOREIGN PATENT DOCUMENTS

| KR | 200229825 | 7/2001 |
| KR | 1020020014063 | 2/2002 |
| KR | 200289676 | 9/2002 |

\* cited by examiner the various figures and embodiments of the present invention.

METHOD FOR PREPARING PELLETS FROM RICE HUSK AND APPARATUS FOR REMOVING ODOR USING RICE HUSK PELLET BIO-MEDIA

BACKGROUND OF THE INVENTION

1. Field of the Invention

Exemplary embodiments of the present invention relate to a method for preparing pellets from rice husk and an apparatus for removing odor using rice husk pellet bio-media; and, more particularly, to a method for preparing cylindrical rice husk pellets, including grinding rice husk, a by-product of rice milling, and extruding the ground rice husk with a binder through an extruder at high temperature, and to an apparatus for removing atmospheric odor using the prepared rice husk pellets as bio-media.

2. Description of Related Art

In biological deodorization methods which have recently attracted attention, materials for media on which microorganisms grow include ceramics, wood barks, porous polymer media, etc. However, the existing media have problems in that water and nutrients essential for the growth of microorganisms should be supplied in order for each medium to be used as a bio-medium and also that a decrease in pH of water caused by the oxidation of odor-causing compounds leads to the death of microorganisms.

In an attempt to solve the problems associated with the existing bio-media, Korean Patent Registration No. 0375163 discloses a biological deodorization method employing rice husk and rice-straw and an apparatus for carrying out the method. According to the disclosure of the Korean Patent, the problem that the pH of spray water decreases is overcome by using rice husk as media for providing a carbon source to microorganisms and oxidizing odor-causing compounds and by using rice-straw as microbial media carrier for reducing oxidized odor compounds. Also, micronutrients released from each of the media act as nutrients essential for the growth of microorganisms to eliminate the need to supply external carbon sources and nutrients.

However, in the above Korean Patent, the particle size of rice husk, a by-product of rice milling, is as small as about 0.5 cm or smaller, a water film is formed in pores between rice husk particles after water spray, and as the operating time becomes longer, the rice husk layer settles under load to reduce the porosity of the rice husk layer. For these reasons, there is a problem in that, when odor-containing air is introduced, a great pressure loss and channeling occur. In addition, there is a problem in that the structure of the apparatus is complex, because, in order to prevent the pH of circulating spray water from decreasing, rice-straw and rice husk are placed separately in a water bath for reduction and a water bath for oxidation, respectively, such that the water baths are operated separately.

SUMMARY OF THE INVENTION

An embodiment of the present invention is directed to a method for preparing pellets from rice husk, including grinding rice husk and compressing the ground rice husk with a binder to high density.

Another embodiment of the present invention is directed to an apparatus for removing odor using rice husk pellet bio-media prepared in accordance with the method of the present invention, wherein the rice husk pellets have uniform porosity and may contain a large amount of water so as to function as bio-media to which microorganisms can adhere, and also wherein a high concentration of an organic matter eluted from the rice husk pellets during water supply serves as an alkalinity source, such that a decrease in the pH of circulating spray water does not occur over a long period of time, and further wherein the operating time of the apparatus can further be extended by supplying chemicals, and an odor removal operation may be carried out in one reactor without needing a water bath for reduction.

Other objects and advantages of the present invention can be understood by the following description, and become apparent with reference to the embodiments of the present invention. Also, it is obvious to those skilled in the art to which the present invention pertains that the objects and advantages of the present invention can be realized by the means as claimed and combinations thereof.

In accordance with an embodiment of the present invention, there is provided a method of preparing pellets from rice husk, including: grinding rice husk; adding ammonia water to a mixture of ethylene vinyl acetate and poly(vinylacetate) to prepare a mixed liquid binder; mixing the mixed mixture with the ground rice husk to obtain a binder/rice husk mixture; extruding the binder/rice husk mixture through an extruder; and cooling the extruded mixture at room temperature.

In accordance with still another embodiment of the present invention, there is provided an apparatus for removing odor using rice husk pellet bio-media prepared in accordance with the above-described method of the present invention, the apparatus including: a circulating spray water reservoir; a spray water pump connected to the circulating spray water reservoir and serving to move circulating spray water; an odor air blower for injecting an odor air; a bed layer of rice husk pellets located upstream of an odor air supply region into which the odor air is injected by the odor air blower; and a circulating spray water injection nozzle located above the bed layer of rice husk pellets.

DESCRIPTION OF SPECIFIC EMBODIMENTS

Figure 1:
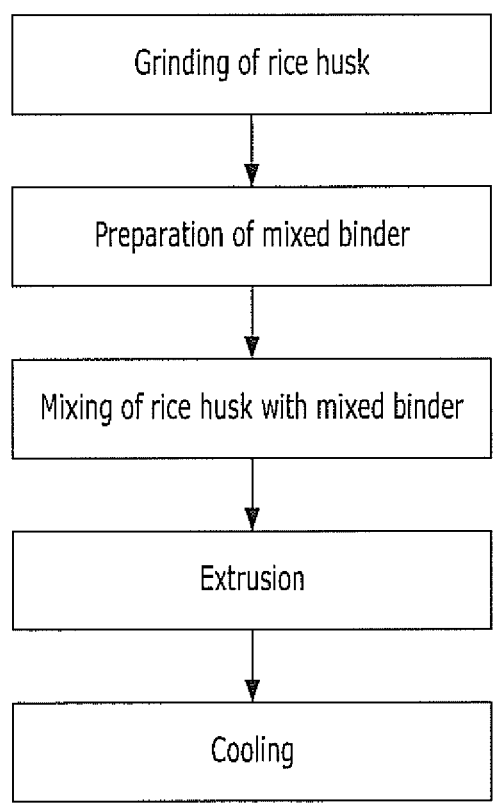
FIG. 1 is a flow chart schematically showing a method for preparing rice husk pellets in accordance with an embodiment of the present invention.

Exemplary embodiments of the present invention will be described below in more detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Throughout the disclosure, like reference numerals refer to like parts throughout the various figures and embodiments of the present invention.

The method of preparing pellets from rice husk according to the present invention includes: grinding rice husk; adding ammonia water to a mixture of ethylene vinyl acetate and poly(vinylacetate) to prepare a mixed liquid binder; mixing the mixed binder with the ground rice husk to obtain a binder/ rice husk mixture; extruding the binder/rice husk mixture through an extruder; and cooling the extruded mixture at room temperature.

Also, the rice husk may be ground to a particle size of 1 mm or less, and the binder/rice husk mixture may be extruded through the extruder maintained at a temperature between 80° C. and 90° C.

Moreover, in the adding ammonia water to the mixture of ethylene vinyl acetate and poly(vinylacetate), the mixing ratio of ethylene vinyl acetate:poly(vinylacetate):ammonia water may be 1:1:0.1. Moreover, the mixing ratio of the mixed binder:the ground rice husk may be 10:2.

Another embodiment of the present invention is an apparatus for removing odor using rice husk pellet bio-media prepared in accordance with the above-described method of the present invention, the apparatus including: a circulating spray water reservoir; a spray water pump connected to the circulating spray water reservoir and serving to move circulating spray water; an odor air blower for injecting an odor air; a bed layer of rice husk pellets located upstream of an odor air supply region into which the odor air is injected by the odor air blower; and a circulating spray water injection nozzle located above the bed layer of rice husk pellets.

The rice husk pellet may have a cylindrical shape having a diameter of 2 cm and a length of 3 cm.

Hereinafter, the construction, function and effect of preferred embodiments of the method for preparing pellets from rice husk according to the present invention and the apparatus for removing odor using the rice husk pellet bio-media will be described in detail.

FIG. 1 is a flow chart schematically showing a method for preparing rice husk pellets in accordance with an embodiment of the present invention. As shown therein, the method for preparing pellets from rice husk includes: grinding rice husk; adding ammonia water to a mixture of ethylene vinyl acetate and poly(vinylacetate) to prepare a mixed liquid binder; mixing the mixed binder with the ground rice husk to obtain a binder/rice husk mixture; extruding the binder/rice husk mixture through an extruder; and cooling the extruded mixture at room temperature.

The grinding of rice husk may be carried out by ball milling. Also, the mixed liquid binder is prepared in the following manner. First, water-soluble ethylene vinyl acetate (EVAc) and poly(vinylacetate) (PVAc) are mixed with each other.

More specifically, if gum-state ethylene vinyl acetate and highly viscous poly(vinylacetate) are combined with each other and water is added thereto, the ethylene vinyl acetate will be dissolved, but the poly(vinylacetate) will be set, thus making it impossible to mix the two components. On the contrary, if ammonia water that is an alkaline solution is added to the EVAc/PVAc mixture, the PVAc will also be dissolved so that the mixed binder of ethylene vinyl acetate and PVAc will be uniformly mixed with the ground rice husk. Herein, the mixing weight ratio of ethylene vinyl acetate:poly(vinylacetate):ammonia water (30%) may be 1:1:0.1, and the mixing ratio of the mixed binder and the ground rice husk may be 10:2 by weight ratio.

Then, the mixture of the ground rice husk and the binder is placed in an extruder maintained at a temperature between about 80° C. and 90° C. In the extruder, the mixed binder is melted and more uniformly mixed with the ground rice husk, and the melted binder induces slippage during extrusion to facilitate extrusion. Also, in the high-temperature extrusion process, ammonia evaporates as gas, and thus the produced rice husk pellets are soft in the initial stage after extrusion and become hardened after they have been cooled at room temperature. When the pellets after being hardened are immersed in water, the ethylene vinyl acetate component will absorb a large amount of water due to its hydrophobic nature so as to be swollen, and the poly(vinylacetate) component from which the ammonia component evaporated will strongly fix the ground rice husk particles, thereby providing pellets contain water and, at the same time, are soft and elastic.

When raw rice husks are used as bio-media for odor removal, there are problems in that influent odor gas is difficult to uniformly pass through the rice husk bed layer, because the number of pores between the rice husk particles is small such that the rice husk bed layer is blocked by microorganisms, and water films are formed in the pores. In addition, there is problem in that, as the operating time become longer, the rice husk bed layer settles. According to the present invention, such problems can be solved by grinding raw rice husk and compressing the ground rice husk with a binder to form pellet bio-media.

Odor gases such as ammonia and sulfide gases are oxidized to nitrate or nitrite or sulfate ions by microorganisms in water, so that the alkalinity of circulating spray water is consumed and the pH of circulating spray water is lowered to the acidic range. If the pH of circulating spray water is lowered to 6 or less, the metabolism of nitrifying bacteria will be inhibited due to a lack of alkalinity, so that the concentration of ammonia in circulating spray water will be increased to produce odor gas. For this reason, for the biological oxidation of ammonia gas, it is required to continuously supplement alkalinity with an inorganic carbon source.

In order to continuously supplement alkalinity, according to the present invention, rice husk is ground and prepared into pellets. The prepared pellets have a density which is about 30 times higher than that in Korean Patent Registration No. 0375163 in which raw rice husk is used as bio-media. Accordingly, the pellets of the present invention can supplement alkalinity for a long period of time, and thus allows the odor removal apparatus to be operated for a long period of time without lowering the pH of circulating spray water. In addition, when carbon components in the rice husk pellets are completely eluted and exhausted, a mixture of sodium carbonate ($Na_2CO_3$) and sodium hydrogen carbonate ($NaHCO_3$) as alkaline agents, mixed at a molar ratio of 1:2 or more, may be introduced so that they can act as a carbon source for the growth of bacteria and as an alkalinity source, whereby the odor removal apparatus can be operated for a more extended period of time without lowering the pH of circulating spray water. Sodium carbonate and sodium hydrogen carbonate coexist as the electron donor carbonate ($CO_3^{--}$) and the electron acceptor hydrogen carbonate ($HCO_3^-$), so that they are used not only as a buffer to inhibit the change in pH of water, but also as a carbon source for nitrifying bacteria that grow using inorganic carbon ($CO_2$).

Accordingly, by using rice husk pellets (obtained by compressing rice husk) as bio-media and by additionally using sodium carbonate and sodium hydrogen carbonate, circulating spray water can be used for a long period of time, and as a result, odor removal can be achieved even by one spray water reservoir without needing to place a separate water bath for reduction.

Hereinafter, an apparatus for removing odor using the rice husk pellet bio-media prepared according to the above-described method will be described in detail.

Figure 2:
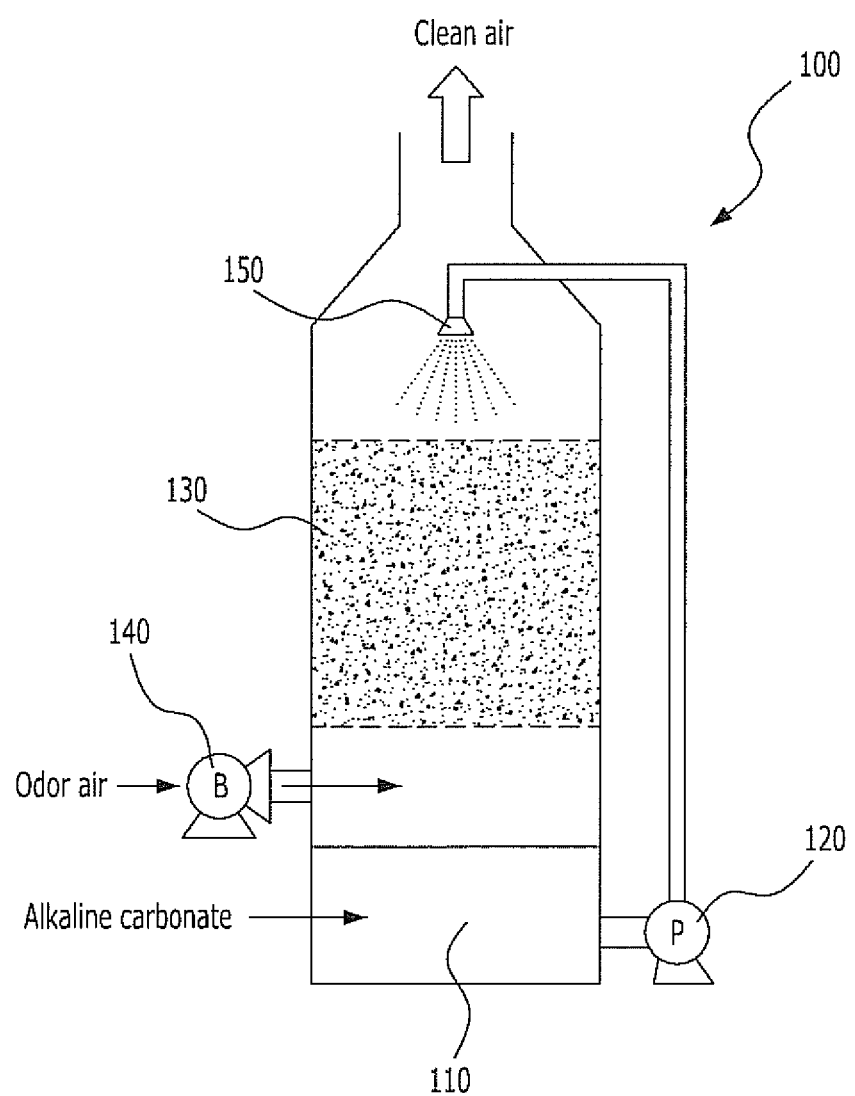
FIG. 2 schematically shows the structure of an apparatus for removing odor using rice husk pellet bio-media in accordance with an embodiment of the present invention.
Figure 3:
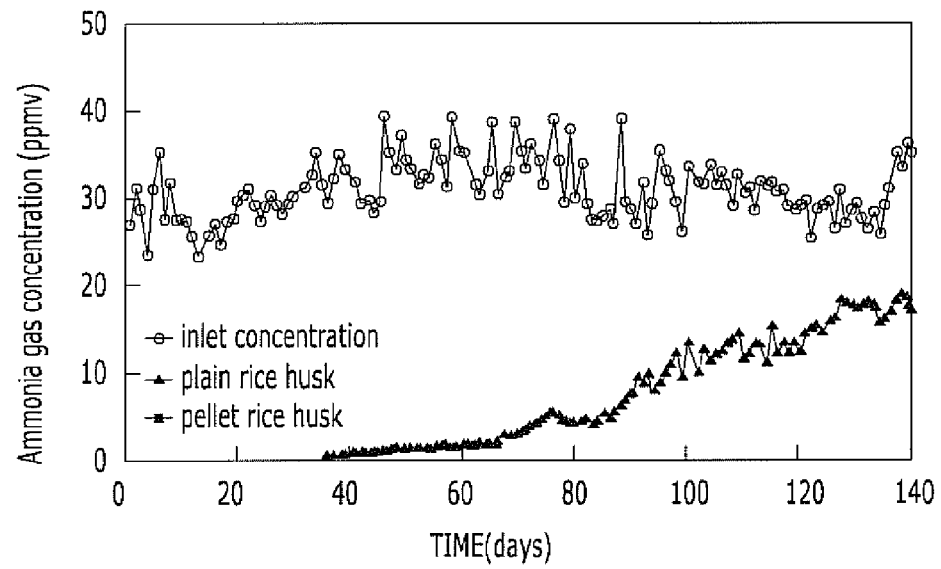
FIGS. 3 to 6 show the results of measuring the outlet gas concentrations and the changes in pH and alkalinity of spray water.
Figure 4:
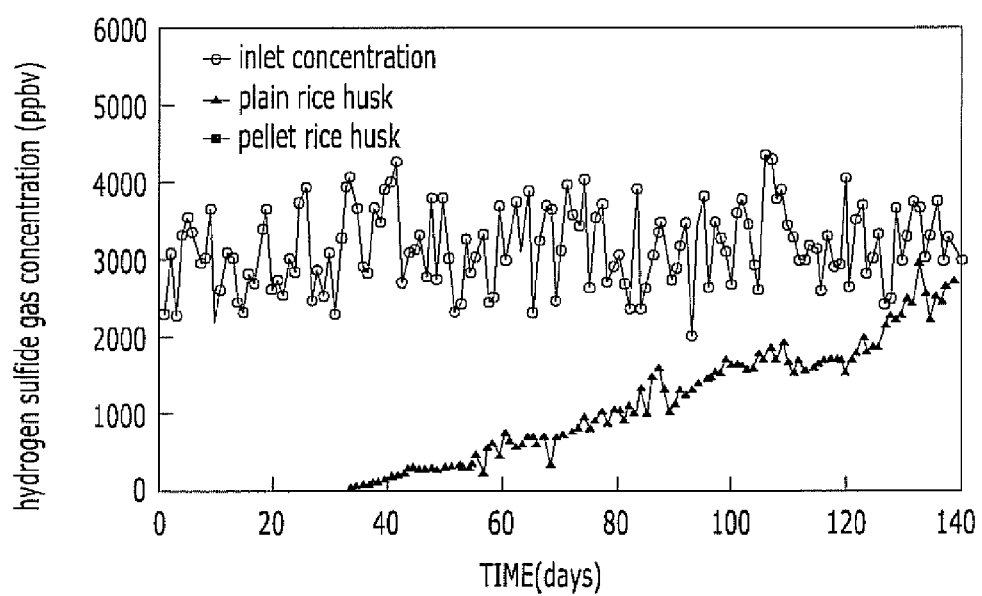
Figure 5:
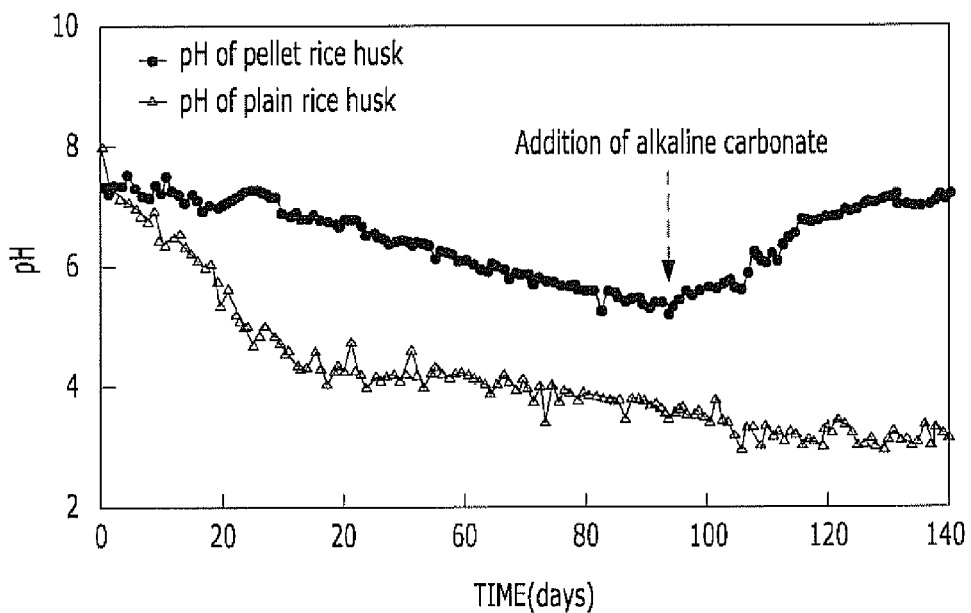
Figure 6:
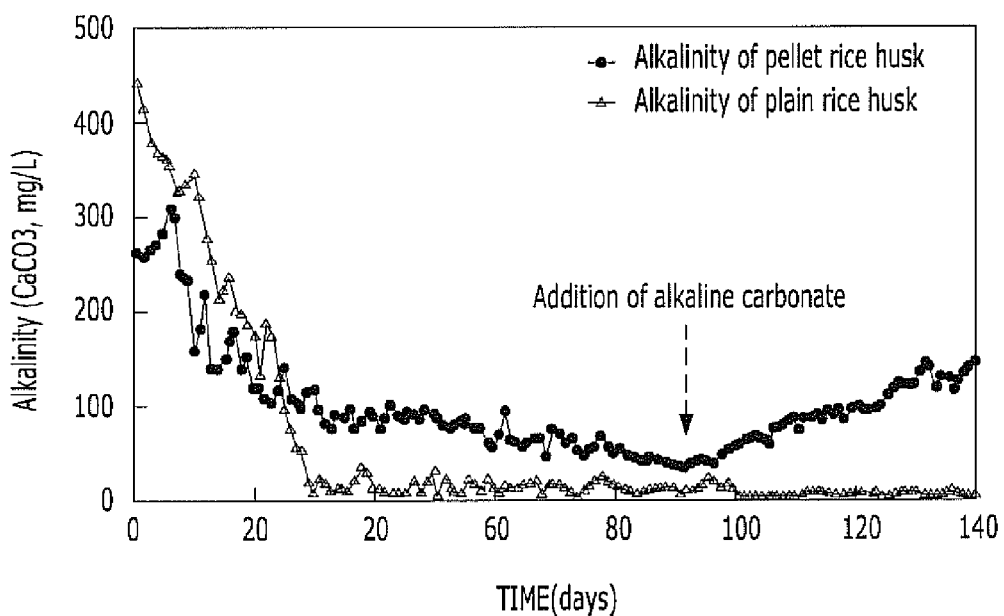

FIG. 2 schematically shows an apparatus for removing odor using rice husk pellet bio-media according to the present invention.

As shown in FIG. 2, an odor removal apparatus 100 according to the present invention includes a circulating spray water reservoir 110, a spray water pump 120, an odor air blower 140, a bed layer of rice husk pellet media 130, and a circulating spray water injection nozzle 150.

The circulating spray water reservoir 110 serves to store circulating spray water, and the spray water pump 120 serves to spray circulating spray water to the bed layer of rice husk pellet media 130. Also, the odor air blower 140 serves to inject odor air, and the bed layer of rice husk pellet media 130 is located such that it is supported by a mesh-shape member upstream of an odor air supply region into which odor air is injected by the odor air blower 140. Furthermore, the circulating spray water injection nozzle 150 is placed above the bed layer of rice husk pellet media 130 and serves to inject circulating spray water.

The above-described elements are arranged in a vertical direction and included in a body.

In the apparatus constructed as described above, the rice husk swell upon water absorption to become elastic, and carbon, phosphorus and the like required for microbial growth are eluted from the rice husk pellets and contained in water in the circulating spray water reservoir 110.

Also, when spray of water to the bed layer of rice husk pellet media 130 is continued, atmospheric microorganisms adhere to and live on the surface of the rice husk pellets. When an odor air containing ammonia and sulfide gases is injected by the blower 140 and moved upward to contact with the rice husk pellet which has microorganisms attached thereto, the ammonia and sulfide gases are adsorbed and oxidized by the microorganisms to nitrate nitrogen and sulfate, and an odor-free clean air is discharged from the odor removal apparatus.

When the nitrate nitrogen and sulfate oxidized in the bed layer of rice husk pellet media 130 is washed by the downwardly sprayed water and accumulated in the circulating spray water reservoir 110, the pH and alkalinity of circulating spray water in the reservoir are lowered. However, due to the supply of alkalinity by carbon components which are continuously eluted from the rice husk pellets, the pH-lowering rate is very slow. After alkalinity resulting from the rice husk pellets has been completely exhausted, when an alkaline carbonate mixture of sodium carbonate and sodium hydrogen carbonate as a buffer to inhibit the change in pH of water is introduced into the circulating spray water reservoir, it is possible to continuously treat odor gas without lowering the pH of circulating spray water.

Also, at a microbial inoculation stage, spray water is sprayed at high frequency, but after microbial inoculation, spay water may be sprayed 2-3 times a day, because the rice husk pellets are made such that they contain water.

Accordingly, the process of removing odor using the rice husk pellet media of the present invention is as follows. An odor air is introduced through the blower 140 into the odor removal apparatus, and the introduced odor air is moved upward, and then the odor components of the odor air are oxidized by microorganisms attached to the bed layer of rice husk pellet media 130, while a clean air is discharged from the apparatus. The odor gas oxidized in the bed layer of pellet media is washed by the sprayed water and accumulated in the circulating water spray reservoir 110. Water in the circulating spray water reservoir 110 is treated with carbon sources eluted from the rice husk pellets by water spray, and then is treated with alkaline carbonates which are additionally supplied.

Hereinafter, the results of comparative experiments carried out in the present invention will be described. In the present invention, plain rice husk and rice husk pellets containing a binder were compared to each other with respect to water content upon introduction of odor air, head loss according to air flow rate, the ability to prevent the pH of spray water from decreasing due to the oxidation of ammonia gas and sulfide gas, and the ability to remove odor gas.

In order to carry out the comparative experiments, a cylindrical acrylic column having a diameter of 10 cm and a height of 1.2 m was divided into an odor gas chamber having a height of 30 cm, a water spray chamber having a height of 30 cm and a rice husk media layer having a height of about 60 cm, and as a circulating spray water reservoir, a vessel having a volume of about 8 L was provided separately from the column. Using this arrangement, circulating spray water was sprayed to the rice husk media layer for 5 minutes at 1-hour intervals.

The same two reactors were used to compare plain rice husk with the bed layer of rice husk pellets. Plain rice husk was used in a raw state and filled in the rice husk media layer, and the pellet rice husk of the present invention was used in a cylindrical shape having a diameter of 2 cm and a length of 3 cm and was filled in the in the rice husk media layer

TABLE 1

| Plain rice husk | | | Pellet rice husk | | |
|---|---|---|---|---|---|
| Initial weight (g) | Weight after water absorption (g) | Increase in weight (%) | Initial weight (g) | Weight after water absorption (g) | Increase in weight (%) |
| 3 | 4.6 | 150 | 3 | 6.2 | 210 |
| 8 | 10.7 | 134 | 8 | 18.4 | 230 |
| 12 | 17 | 140 | 12 | 25.2 | 210 |

Table 1 above compares the water content between plain rice husk and the pellet rice husk after water spray. As can be seen in Table 1, plain rice husk showed an increase in weight of about 140% compared to the initial weight, whereas the pellet rice husk of the present invention showed an increase in weight of about 220% compared to the initial weight. This suggests that the pellet rice husk prepared by mixing the ground rice husk with the mixed binder (ethylene vinyl acetate and poly(vinylacetate) has a very high water content, and thus it can reduce the frequency of water spray and is not dried even when odor air is introduced for a long period of time.

TABLE 2

| Air flow rate (L/min) | Residence time (sec) | Head loss of plain rice husk | Head loss of pellet rice husk |
|---|---|---|---|
| 4 | 60 | 0 | 0 |
| 8 | 30 | 40 mm | 0 |
| 12 | 20 | 30 mm | 1 mm |

Table 2 compares the head loss according to the change in residence time caused by the change in air flow rate between plain rice husk and the pellet rice husk. As can be seen in Table 2, in the case of plain rice husk, the porosity was about 40%, water films were formed in the pores of the rice husk particles, and thus the higher the air flow rate, the higher was the head loss. On the contrary, in the case of the pellet rice husk, the porosity reached about 60-70%, no water film was formed, and thus little or no head loss occurred.

FIGS. 3 to 6 show the results of measuring the outlet gas concentrations and the changes in pH and alkalinity of spray water while injecting an odor air containing 30 ppm ammonia gas and 3 ppm hydrogen sulfide to each of plain rice husk and pellet rice husk with a nominal residence time of 1 minute and operating the apparatus for 140 days under the same conditions as above.

As can be seen in FIGS. 3 to 6, in the case of plain rice husk, the outlet concentrations of ammonia and sulfide gases increased from about 40 days after the start of the experiment, and the odor air treatment efficiency also decreased after that time. This is believed to be because the rice husk bed layer was settled, a channeling phenomenon occurred in the bed layer due to the formation of water films, and also the amount of plain rice husk loaded in the bed was very small, and thus the pH of spray water was rapidly lowered and the alkalinity of spray water was rapidly exhausted.

On the contrary, because the rice husk pellets were standardized to a given size and hard, the porosity thereof did not change even after a long-term operation. Also, because the rice husk pellets were compressed, they could continuously supply alkalinity, and thus allowed odor air to be continuously treated without lowering the pH of circulating spray water. In addition, it can be seen that, if the alkalinity of spray water is exhausted, an inorganic carbon source and an alkaline carbonate as an alkaline supplementing agent may be provided to the spray water to improve the odor air treatment efficiency.

As described above, the embodiment of the present invention provides a method of preparing pellets from rice husk, including grinding rice husk and compressing the ground rice husk with a binder to high density. Also, the present invention an odor removal apparatus including rice husk pellet bio-media prepared in accordance with the method of the present invention, wherein the rice husk pellets have uniform porosity and may contain a large amount of water so as to function as bio-media to which microorganisms can adhere, and also wherein a high concentration of an organic matter eluted from the rice husk pellets during water supply serves as an alkalinity source, such that a decrease in the pH of circulating spray water does not occur over a long period of time, and further wherein the operating time of the apparatus can further be extended by injection of chemicals, and an odor removal operation may be carried out in one reactor without needing a water bath for reduction.

While the present invention has been described with respect to the specific embodiments, it will be apparent to those skilled in the art that various changes and modifications may be made without departing from the spirit and scope of the invention as defined in the following claims.

What is claimed is:

1. A method for preparing rice husk bio-media pellets having a plurality of pores to which microorganisms are attachable, from rice husk, comprising:
   grinding rice husk;
   adding ammonia water to a mixture of ethylene vinyl acetate and poly(vinylacetate) to dissolve the poly(vinylacetate), thereby preparing a mixed liquid binder;
   mixing the mixed liquid binder with the ground rice husk to obtain a binder/rice husk mixture;
   heating the binder/rice husk mixture within an extruder maintained at a temperature between 80° C. and 90° C. and extruding the heated binder/rice husk mixture, thereby forming rice husk bio-media pellets having a plurality of pores to which microorganisms are attachable, wherein the pores of the rice husk bio-media pellets are made by evaporating ammonia gas of the ammonia water through the heating; and
   cooling the rice husk bio-media pellets at room temperature,
   wherein microorganisms are attached to the pores of the rice husk bio-media pellets and fed by carbon components of the rice husk bio-media pellets when the ethylene vinyl acetate of the rice husk bio-media pellets absorbs an amount of water.

2. The method of claim 1, wherein the rice husk is ground to 1 mm or less.

3. The method of claim 1, wherein, in the adding ammonia water to a mixture of ethylene vinyl acetate and poly(vinylacetate), a mixing ratio of ethylene vinyl acetate:poly(vinylacetate):ammonia water is 1:1:0.1.

4. The method of claim 1, wherein a mixing ratio of the mixed liquid binder:the ground rice husk is 10:2.

* * * * *